United States Patent
Giovenzana et al.

(10) Patent No.: US 9,193,659 B2
(45) Date of Patent: Nov. 24, 2015

(54) PROCESS FOR THE IODINATION OF AROMATIC COMPOUNDS

(75) Inventors: Giovanni Battista Giovenzana, Novara (IT); Camilla Cavallotti, Novara (IT); Luciano Lattuada, Bussero (IT); Fulvio Uggeri, Codogno (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 12/918,001

(22) PCT Filed: Feb. 16, 2009

(86) PCT No.: PCT/EP2009/051747
§ 371 (c)(1),
(2), (4) Date: Aug. 17, 2010

(87) PCT Pub. No.: WO2009/103666
PCT Pub. Date: Aug. 27, 2009

(65) Prior Publication Data
US 2010/0331567 A1 Dec. 30, 2010

(30) Foreign Application Priority Data
Feb. 20, 2008 (EP) .................................... 08151661

(51) Int. Cl.
| | |
|---|---|
| C07C 221/00 | (2006.01) |
| C07C 51/363 | (2006.01) |
| C07B 39/00 | (2006.01) |
| C07C 37/62 | (2006.01) |
| C07C 67/307 | (2006.01) |
| C07C 231/12 | (2006.01) |
| C07C 237/46 | (2006.01) |
| C25B 3/06 | (2006.01) |

(52) U.S. Cl.
CPC ............... *C07C 51/363* (2013.01); *C07B 39/00* (2013.01); *C07C 37/62* (2013.01); *C07C 67/307* (2013.01); *C07C 231/12* (2013.01); *C07C 237/46* (2013.01); *C25B 3/06* (2013.01)

(58) Field of Classification Search
CPC .................................................... C07C 221/00
USPC ......................................................... 564/343
See application file for complete search history.

(56) References Cited

U.S. PATENT DOCUMENTS

| | | | |
|---|---|---|---|
| 3,647,864 A | | 3/1972 | Ackerman |
| 3,833,490 A | * | 9/1974 | Bizot et al. ..................... 205/433 |
| 5,013,865 A | | 5/1991 | Cross et al. |
| 5,575,905 A | | 11/1996 | Wistrand et al. |
| 5,728,877 A | * | 3/1998 | Anelli et al. .................. 564/153 |
| 5,763,650 A | | 6/1998 | Mauro et al. |
| 5,763,663 A | | 6/1998 | Anelli et al. |
| 6,420,603 B1 | * | 7/2002 | Alessandroni et al. ....... 564/123 |
| 8,383,868 B2 | | 2/2013 | Yoshida et al. |
| 8,648,223 B2 | | 2/2014 | Yoshida et al. |

(Continued)

FOREIGN PATENT DOCUMENTS

| | | |
|---|---|---|
| CA | 2002599 A1 | 5/1990 |
| CA | 2020489 A1 | 11/2005 |
| CN | 1328539 A | 12/2001 |

(Continued)

OTHER PUBLICATIONS

Miller, Larry L. et al., "Scope and Mechanism of Aromatic Iodination with Electrochemically Generated Iodine (I)", Journal of the American Chemical Society, vol. 98, No. 6, Mar. 17, 1976, pp. 1515-1519, XP002491790, Colorado State University, Fort Collins, Colorado.

(Continued)

*Primary Examiner* — Scarlett Goon
*Assistant Examiner* — Sonya Wright
(74) *Attorney, Agent, or Firm* — VIVICAR Law, PLLC

(57) ABSTRACT

The present invention relates to a process for the preparation of iodinated phenols, —in particular, it relates to a process including the electrochemical iodination of 3,5-disubstituted phenols of formula (1) to the corresponding 3,5-disubstituted-2, 4,6-triiodophenols of formula (2), which are useful intermediates for the synthesis of x-ray contrast media, and to the preparation of the contrast media themselves. Furthermore, the present invention includes the electrochemical iodination of 3, 5- disubstituted anilines of formula (6) to the corresponding 3,5-disubstituted-2,4,6-triiodoanilins of formula (7).

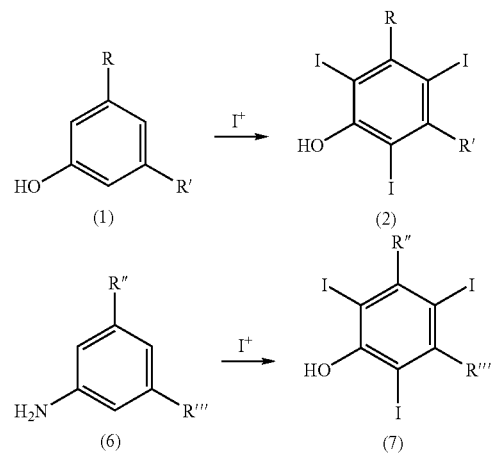

14 Claims, No Drawings

(56) References Cited

U.S. PATENT DOCUMENTS

| | | | |
|---|---|---|---|
| 8,809,602 | B2 | 8/2014 | Yoshida et al. |
| 2008/0146853 | A1 | 6/2008 | Midorikawa et al. |

FOREIGN PATENT DOCUMENTS

| | | | |
|---|---|---|---|
| DE | 124516 | A1 | 3/1977 |
| DE | 68912920 | T2 | 8/1994 |
| EP | 0083964 | A1 | 7/1983 |
| EP | 0365541 | A1 | 5/1990 |
| EP | 0376858 | A | 7/1990 |
| EP | 0773923 | A1 | 5/1997 |
| EP | 0782562 | A1 | 7/1997 |
| EP | 0828705 | A1 | 3/1998 |
| GB | 1548594 | A | 7/1979 |
| GB | 1472050 | A | 4/1997 |
| JP | H01-141803 | A | 6/1989 |
| JP | H01-160804 | A | 6/1989 |
| JP | 10-506653 | A | 6/1998 |
| JP | 11-505827 | A | 5/1999 |
| JP | 2000264605 | A | 9/2000 |
| RU | 2060246 | C1 | 5/1996 |
| RU | 2278816 | C2 | 6/2006 |
| WO | 88-09328 | A1 | 12/1988 |
| WO | 92-14695 | A1 | 9/1992 |
| WO | 94-14478 | A1 | 7/1994 |
| WO | 96-37458 | A1 | 11/1996 |
| WO | 96/37461 | A | 11/1996 |
| WO | 96-37461 | A1 | 11/1996 |
| WO | 97/05097 | A | 2/1997 |
| WO | 97-05097 | A1 | 2/1997 |
| WO | 98-28259 | A1 | 7/1998 |
| WO | 00/32561 | A | 6/2000 |
| WO | 2008-111521 | A1 | 9/2008 |

OTHER PUBLICATIONS

PCT International Search Report for PCT/EP2009/051747, mail date Nov. 4, 2009.
PCT Written Opinion of the International Searching Authority for PCT/EP2009/051747, mail date Nov. 4, 2009.
Third Party Observation for European application No. 09713167.6, mail date Apr. 3, 2012.
PCT International Search Report for PCT/EP2010/059619, mail date Oct. 7, 2010.
PCT Written Opinion of the International Searching Authority for PCT/EP2010/059619, mail date Oct. 7, 2010.
Lines, Robert et al., "Electrophilic Aromatic Substitution by ositive Ioding Species. Iodination of Deactivated Aromatic Compounds", Acta Chemica Scandinavica, Series B: Organic Chemistry and Biochemistry, Munksgaard, Copenhagen, DK, vol. B34, Jan. 1, 1980, pp. 47-51, XP002491791, ISSN: 0302-4369.
First Office Action for Australian application No. 2010270302, mail date Jun. 28, 2013.
First Office Action for Australian application No. 2009216783, mail date Apr. 13, 2012.
First Office Action for Chinese application No. 200980105904.8, mail date Sep. 5, 2012 (English translation).
Office Action for European application No. 09713167.6, mail date Sep. 16, 2011.
Office Action for European application No. 09713167.6, mail date Mar. 20, 2013.
Office Action for New Zealand application No. 586944, mail date Oct. 20, 2011.
Decision on Grant of Patent for Invention for application No. RU201038570/04, mail date Jul. 31, 2012 (English translation).
Search Report and Written Opinion for Singaporean application No. SG201108724-4, mail date Aug. 10, 2012.
Office Action for JP2010-547157, mail date Mar. 12, 2013, and English translation.
First Office Action for Chinese application No. 201080027573.3, mail date Nov. 12, 2013 (English translation).
Alemi, Abdolali et al., "The Novel Route for Synthesis of Tellurium Tetrachloride, and Redetermination of Its Structure at Lower Temperature by X-Ray Crystallography", Acta Chim. Slov., vol. 47, 2000, pp. 89-98.
Greene, Theodora W., "Protective Groups in Organic Synthesis", John Wiley & Sons, 1981, Chapter 2: Protection for the Hydroxyl Group Including 1,2- and 1,3-Diols.
Soled, Stuart et al., Acta Cryst., "The Crystal Structures of KICl2 and KICl2,H2O", 1973, B29, pp. 2104-2109.
The Merck Idex, 13th Edition, Merck & Co., Inc., Whitehouse Station, New Jersey, 2001, item Nos. 5071 and 5073, p. 908-909, ISBN No. 0911910-13-1.
Zittel, H.E. et al., "A Glassy-Carbon Electrode for Voltammetry", Analytical Chemistry, vol. 37, No. 2, 1965, pp. 200-203.
Office Action for Canadian application No. 2,715,430, mail date Jul. 3, 2014.
Office Action for Canadian application No. 2,763,405, mail date Jul. 24, 2012.
Final Office Action for Japanese application No. 2010-547157, mail date Feb. 4, 2014 (English translation).
Office Action for Japanese application No. 2012-518962, mail date May 7, 2014 (English translation).
Office Action for Mexican application No. MX/a/2010/009184, mail date Mar. 10, 2014 (English translation).
Decision on Grant for Russian application No. 2012103998, mail date May 5, 2014 (English translation).
Office Action for Canadian application No. 2,715,430, mail date Apr. 23, 2015.
Office Action for Israeli application No. 207640, mail date Mar. 12, 2015 (English translation).
Office Action for European application No. EP09713167.6, mail date May 11, 2015.
Office Action for Indian application No. 5769/CHENP/2010, mail date Feb. 26, 2015.
Office Action: Notice of Allowance for U.S. Appl. No. 13/375,797, mail date Mar. 17, 2015.
Office Action for Mexican application No. MX/a/2010/009184, mail date Dec. 19, 2014 (English translation).
Office Action-Second for New Zealand application No. 596447, mail date Oct. 1, 2012.
Office Action-Third for New Zealand application No. 596447, mail date Oct. 18, 2013.
Office Action for Korean application No. 10-2010-7017162, mail date Jun. 1, 2015 (English translation).

\* cited by examiner

PROCESS FOR THE IODINATION OF AROMATIC COMPOUNDS

This application is the national stage application of corresponding international application number PCT/EP2009/051747 filed Feb. 16, 2009, which claims priority to and the benefit of European application no. 08151661.9, filed Feb. 20, 2008, all of which are hereby incorporated by reference.

The present invention relates to a process for the preparation of iodinated aromatic compounds. In particular, it relates to a process including the electrochemical iodination of 3,5-disubstituted phenols to the corresponding 3,5-disubstituted-2,4,6-triiodophenols, which are useful intermediates for the synthesis of x-ray contrast media, and to the preparation of the contrast media themselves.

BACKGROUND

Iodinated contrast media are well-known compounds widely used in x-ray imaging diagnostic techniques. Suitable examples of the said compounds include, for instance, diatrizoate, iothalamate, ioxithalamate, metrizoate, iohexol, iomeprol, iopamidol, iopentol, iopromide, ioversol, ioxilan, iodixanol, iosarcol, iogulamide, ioglunide, iogluamide, acetrizoate, iodamide, iocetamide and metrizamide, which are all monomeric; while, for example, ioxaglate, iotrolan, iotasul, iodipamide, iocarmate, iodoxamate, iotroxate, iotrolan, and the like, are dimers. Other examples of iodinated contrast agents are described, for instance, in WO 94/14478 (Bracco).

As a common feature, their chemical structure shares a triiodinated aromatic nucleus which provides the enhanced contrast effect.

The said compounds may be prepared by a variety of routes, some of which comprise the aromatic iodination of given substrates, in particular suitable anilines, so as to provide the corresponding 2,4,6-triiodoaniline derivatives, to be further converted and processed to the final compounds.

Useful precursors for the preparation of the above compounds are also 3,5-disubstituted phenols, which undergo triiodination on the available 2, 4 and 6 positions, at first, so as to give rise to the corresponding 3,5-disubstituted-2,4,6-triiodophenols. These latter, in turn, may be further converted and processed through the so-called Smile's rearrangement, to the expected final compounds.

For a general reference to the above synthetic route and Smile's rearrangement see, for instance, WO 88/09328, WO 97/05097 and WO 00/32561 (Bracco).

Iodination on the phenol ring may occur at the ortho and para free positions, i.e. at the 2, 4 and 6 positions, according to the well-known electrophilic substitution mechanism, thus leading to the triiodinated ring.

The iodination step, in particular, may be performed according to several methods known in the art.

For instance, it can be carried out by using solutions of iodine chloride (ICl) in concentrated hydrochloric acid (HCl) or, alternatively, by means of analogous iodinating agents such as, for instance, $KICl_2$ or $NaICl_2$ in aqueous solution; see, for a general reference, WO 92/14695 (Guerbet) or U.S. Pat. No. 5,013,865 (Mallinckrodt).

The above methods suffer from major drawbacks due to the limited storage life of the iodinating agents and to their corrosive properties. In addition, the presence of chlorine atoms may lead to side-reactions and, thus, to the undesired formation of chlorine side-products, which may affect reaction yields and purity of the final compounds.

The above problems may be well addressed according to an alternative path comprising electrochemical iodination of suitable aromatic nuclei. Electrochemical iodination involves, in particular, the anodic formation of $I^+$ ions from an iodine source, for instance $I_2$ itself, in an electrolytic cell, substantially as per the following Scheme:

and the thus formed $I^+$ cations may then act as iodinating agents on the aromatic nucleus of the targeted compound.

Apart from molecular iodine, a variety of iodides such as alkali metal iodides and even hydriodic acid or their mixtures may be employed as well to electrochemically originate $I^+$ species.

Remarkably, however, electrochemical iodination from $I_2$ source advantageously provides for two moles of iodinating species originating from 1 mole of iodine source. In addition, another main advantage offered by said method is that the iodinating specie may be generated on need, thus avoiding the storage of corrosive reagents. Moreover, as no chlorine source is present, no chlorination by-products affecting the purity of the final compound may be thus obtained.

The electrochemical iodination of aromatic substrates is known in the art as reported, for instance, in J. Am. Chem. Soc., Vol. 98, No. 6, 1976, pages 1515-1519; and EP 828705 (Nycomed Imaging As).

According to EP 828705, in particular, it is disclosed a process for the preparation of monomeric or dimeric triiodoaniline compounds comprising the electrochemical iodination of 3,5-disubstituted anilines or 3,3'-disubstituted-5,5'-linked bisanilines.

As far as phenols and derivatives thereof are concerned, instead, U.S. Pat. No. 3,833,490 discloses a process for the preparation of herbicides comprising the electrochemical iodination of 4-hydroxybenzonitrile in the presence of $IO^-$ ions, so as to provide the corresponding mono- or di-iodinated derivatives bearing iodine atoms in positions 3 and/or 5.

Remarkably, the above iodination process is directly carried out within the electrolytic cell, that is under the oxidizing conditions existing at the anodic compartment, as the presence of a substituent (e.g. cyano group) in para position with respect to the phenolic hydroxy group may render the above substrate less susceptible of oxidative degradation.

However, by even carrying out the iodination step outside the electrolytic cell, the iodination of phenol with a iodinating specie electrochemically generated, did not provide the expected results as mixtures of byproducts were instead obtained. Experimental evidence for the same can be found in Comparative Examples 1 and 2 of the following experimental section.

Despite these major drawbacks concerning the electrochemical iodination of phenols, however, we have unexpectedly found that the electrochemical iodination of given 3,5-disubstituted phenols enabled for the preparation of the corresponding triiodinated compounds.

OBJECT OF THE INVENTION

The present invention thus provides a process for the electrochemical iodination of 3,5-di-substituted phenols and, also, a method for the preparation of x-ray contrast agents including the above electrochemical iodination step.

It is therefore a first object of the present invention a process for the preparation of 3,5-disubstituted-2,4,6-triiodophenols of formula (2), which process comprises:

(a) electrochemically generating I⁺ cations from a suitable iodine source; and
(b) iodinating 3,5-disubstituted-phenols of formula (1) in the presence of the above I⁺ cations of step (a):

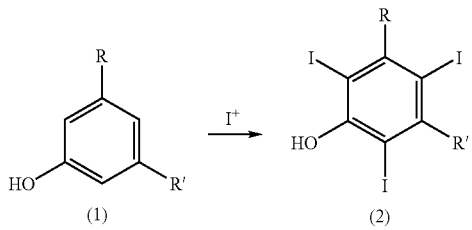

wherein
R and R' represent, the same or different from each other, a group selected from carboxy —COOH, carboxyester —COOR$^1$ and carboxamido —CONH$_2$, —CONHR$^1$ or —CONR$^2$R$^3$; wherein R$^1$, R$^2$ and R$^3$ represent, the same or different from each other, a straight or branched $C_1$-$C_6$ alkyl group which is optionally substituted by one or more groups selected from hydroxy, amino, sulphydryl, $C_1$-$C_6$ alkoxy or carboxy, and/or optionally interrupted by one or more divalent groups selected from —NH—, —O—, >C═O, —(C═O)O—, —O(C═O)—, —NH(C═O)—, —(C═O)NH—, >SO or >SO$_2$ groups.

The present process enables, advantageously, the recovery of triiodinated 3,5-disubstituted phenols of formula (2) in high yields and purity.

In the present description, unless otherwise provided, with the term straight or branched $C_1$-$C_6$ alkyl group we intend a linear or branched alkyl chain with from 1 to 6 carbon atoms. Suitable examples for the said alkyl groups may thus comprise methyl, ethyl, n-propyl, isopropyl, n-butyl, isobutyl, sec-butyl, tert-butyl, n-pentyl, n-hexyl, and the like.

The above alkyl groups may be further substituted and/or interrupted by a variety of moieties as set forth above.

Within them, with the term $C_1$-$C_6$ alkoxy we intend any alkyl-oxy group wherein the alkyl moiety just represents any of the above straight or branched $C_1$-$C_6$ alkyl groups. Suitable examples of alkoxy groups of the invention may thus comprise methoxy, ethoxy, n-propoxy, isopropoxy, n-pentyloxy, and the like.

According to a preferred embodiment of the process of the invention, within the compounds of formula (1) and (2), R and R' represent, the same or different from each other, a group selected from carboxy (—COOH), carboxyester (—COOR$^1$) and carboxamido (—CONH$_2$, —CONHR$^1$ or —CONR$^2$R$^3$) wherein R$^1$, R$^2$ and R$^3$ are, the same or different from each other, a straight or branched $C_1$-$C_4$ alkyl group optionally substituted by one or more hydroxy groups.

Even more preferably, within the compounds of formula (1) and (2), R and R' represent, the same or different form each other, a group selected from:
—COOH,
—COOCH$_3$,
—COO(CH$_2$)$_3$—CH$_3$,
—CONH$_2$,
—CONHCH$_3$,
—CONHCH$_2$—CH(OH)—CH$_2$(OH),
—CONHCH[CH$_2$OH]$_2$ From all of the above, as both R and R' groups do not take direct part to the reaction step, as per the details below, it is clear to the skilled person that optional substituents or groups, anyway present within the meanings of R and R' and which may undergo unwanted side reactions, need to be suitably protected before reaction takes place. Protection and subsequent deprotection of the said groups can be accomplished by a variety of methods widely known in the art and conventionally adopted in organic synthesis techniques. For a general reference to protective groups in organic chemistry see, for instance, T. W. Green, Protective Groups in Organic Synthesis (Wiley, N.Y. 1981). The electrochemical generation of I⁺, as per step (a) of the process of the invention is performed in an electrolytic cell, hence in the presence of an anode and a cathode otherwise referred to as anodic and cathodic compartments.

Suitable anodes are those conventionally known in the art and may comprise graphitic carbon anodes, vitreous carbon anodes, platinum anodes or even platinum alloys anodes which alloys may include other metals such as, for instance, iridium, titanium or conductive titanium dioxide. Particularly preferred are platinum and graphitic carbon anodes.

As the cathode, conventional ones may be employed as well including, for instance, carbon, platinum, palladium, lead, copper or stainless steel cathodes as well as mixtures thereof. Carbon and steel cathodes in particular, are the most preferred.

Cathode and anode are electrochemically interconnected according to conventional means, by a porous barrier or diaphragm, for instance consisting of a porous frit or of any other permeable membrane material known in the art for the intended purpose.

According to the process of the invention, the iodinating specie is represented by iodine cations (I⁺) that are generated in situ from any suitable iodine source, for instance comprising molecular I$_2$ or suitable iodide derivatives like the alkaline salts NaI or KI or even hydriodic acid, or any mixture of them.

Within the present invention, molecular iodine (I$_2$) is particularly preferred. Because of the stoichiometry of the reaction the present process refers to, at least 3 moles of the reactive (I⁺) specie are required for each mole of aromatic substrate of formula (1) to be triiodinated to the corresponding compound of formula (2).

Preferably, a slight excess of the iodinating agent to the phenolic substrate will be employed so that the equivalent ratio between them may vary from 1:1 to 3:1 or, even more preferably, from 1:1 to 2:1. semicelle contenuti diversi The anodic reaction is carried out in the presence of an organic solvent, preferably a polar and/or protic solvent such as, for instance, acetonitrile, lower alcohols $C_1$-$C_4$ and mixtures thereof.

Preferably, the process is carried out in the presence of lower alcohols wherein methanol is even more preferred.

Hydroalcoholic solvent systems comprising relevant amounts of water, for instance water:methanol mixtures in a weight ratio of 1:1 or with an even lower water content, for instance of 1:4, should be preferably avoided.

To this extent, particularly when generating the reactive (I⁺) specie in step (a) from molecular iodine, either alone or together with any suitable iodide, the presence of amounts of water that may impair its solubility in the solvent medium, appears to negatively affect the reaction outcome.

As per Comparative example 3, in fact, when the electrochemical oxidation of iodine, as per step (a) of the process, is carried out with the given water:alcohol mixture, major amounts of unreacted iodine are recovered at the end of the process.

As far as the cathodic compartment is concerned, instead, the above limitations on the choice of the solvent system are not needed and, hence, varying amounts of water may be successfully employed.

Typically, polar and/or protic solvents such as acetonitrile, lower alcohols and water admixtures thereof, may be employed.

Among them, methanol-water mixtures are particularly preferred.

The reaction medium is usually kept to an acidic pH, i.e. below 7, through acid addition, for instance of concentrated nitric or sulfuric acid, e.g. 97% $H_2SO_4$. Preferably, pH is kept between 0 and 4 and, even more preferably, between 1 and 2.

Alternatively, step (a) may be performed in the presence of known compounds suitable to maintain conductivity within the electrolytic cell, and thus used for the above purpose.

For the electrochemical generation of $I^+$ cations at the anode, a voltage across the electrodes may be applied, so as to have an anode potential from about 1 to about 3 V versus SCE (Saturated Calomel Electrode as the reference electrode).

Preferably, the reaction is carried out with an anode potential comprised from about 1.2 to about 1.8 V vs. SCE.

Alternatively, the electrolytic process according to the present invention may be performed in a galvanostatic mode, i.e. a constant current is passed through the solution during the process, for instance corresponding to 1-500 mA/cm$^2$.

The temperature during the process is kept constant, for instance between 15° C. and 25° C. by operating according to conventional methods. Typically, as the heat generated during the process may lead to a partial evaporation of the solvent, particularly when employing lower boiling solvents like methanol, additional amounts of fresh solvent may be added so as to keep steady both temperature and solvent volume.

The resulting solution containing the iodinating specie is then contacted with the aromatic substrate (1), or a suitable solution thereof, as formerly indicated.

Typically, as reported in the experimental section, the iodination of the aromatic substrate of formula (1) is carried out in a separate reactor, wherein both the iodinating solution from step (a) and the substrate (1), either as such or suitable dissolved in a selected solvent, for instance including those previously indicated, are properly contacted.

Preferably, a solution of the substrate (1) in a lower alcohol, like methanol, is employed.

Subsequent work-up of the reaction mixture may be then accomplished according to conventional techniques widely known in the art so as to isolate and obtain the final compound of formula (2).

As an example, when using molecular iodine to generate ($I^+$) cations, at the end of the reaction any excess of ($I^+$) or $I_2$ could be easily removed according to conventional methods by adding suitable amounts of alkali iodide, for instance KI, so as to form $I_2$ and, then, $KI_3$ complex. Likewise, excess of iodine could be also removed through the addition of sodium sulfite or bisulfite, up to discolouration of the reaction medium. The compounds of formula (1) as starting materials of the process of the invention are known and, if not commercially available per se, may be all prepared according to known methods.

For a general reference to the compounds of formula (1) see, for instance, the aforementioned WO 88/09328, WO 97/05097 and WO 00/32561.

Likewise, any other reactant and/or solvent being employed in the instant process is known and readily available.

Details concerning the process of the invention are reported in the following experimental section for the electrochemical iodination of 3,5-disubstituted phenols according to the present invention, which is however shortly reported below.

A melting pot, otherwise referred to as crucible, is placed inside a crystallizer put on a magnetic stirrer system. A platinum anode is then suspended and placed between the porous frit constituting the bottom of the melting pot, and the inner bottom of the crystallizer.

A suitable amount of an alcoholic solution of the selected iodine source, for example a solution of $I_2$ in methanol, is poured into the crystallizer so that its volume is such to provide the electrochemical contact with the porous frit, and an amount of acid is then added. A suitable amount of an alcohol-water mixture is then poured into the melting pot, followed by the addition of an acid. When the melting pot with its content is dipped into the iodine alcoholic solution, a graphite cathode is introduced into the melting pot and the system is then electrically connected. A constant electrical flow is maintained, then hydrogen forms at the cathode and the iodine solution turns brown to yellow-orange. During the reaction, a suitable amount of fresh methanol is added portionwise to the anodic compartment so as to compensate evaporation and to keep a permanent contact between the glass frit of the melting pot and the surrounding iodine solution. After a suitable time, for instance of about three hours, the solution is yellow-pale. Then, electric power is stopped and the iodinating solution in the crystallizer is transferred into a one-neck flask. A suitable amount of the selected compound of formula (1) or of a solution thereof is then added, either as such or portionwise, and the mixture is heated under reflux. The reaction is monitored by TLC and heating is continued up to quantitative conversion. The final solution thus obtained is lead cooling to room temperature.

Then, any excess of I+ and $I_2$ may be eliminated by addition of suitable solutions of KI and of a saturated solution of $NaSO_3$ being added up to decolourisation. The solvent is then evaporated and the residue is extracted with a suitable solvent, for instance ethyl acetate. The solution is dried, filtered and evaporated to residue. The crude is purified by flash chromatography onto silica gel or by elution onto a hydrophobic polymeric resin column, starting elution with water to eliminate iodine salts and then with a suitable solvent, for instance acetone, to elute the product.

Once obtained, the compounds of formula (2) may be then easily converted into the corresponding x-ray contrast agents of interest having formula (5) below.

Hence, it is a further object of the present invention a process for the preparation of the compounds of formula (5) below which process comprises:

(a) electrochemically generating $I^+$ cations from a suitable iodine source; and (b) iodinating 3,5-disubstituted-phenols of formula (1) in the presence of the above $I^+$ cations of step (a):

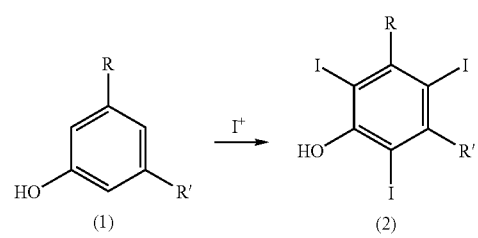

wherein R and R' have the meanings above reported, so as to obtain the compounds of formula (2);

(c) reacting the compound of formula (2), either as such or wherein the hydroxy group on the benzene ring is present as alkali or alkali-earth metal salt, with a compound of formula (3)

R⁴HN(C=O)CH(R⁵)Z          (3)

wherein R⁴ and R⁵ are, the same or different from each other, hydrogen or a straight or branched $C_1$-$C_6$ alkyl group optionally substituted by one or more hydroxy or $C_1$-$C_6$ alkoxy groups and Z is a halogen atom or any suitable leaving group; so as to obtain a compound of formula (4)

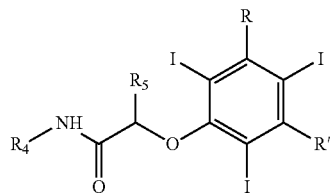

(4)

wherein R, R', W and R⁵ have the above reported meanings; and (d) subjecting the compound of formula (4) to Smile's rearrangement in the presence of bases, so as to obtain the final compound of formula (5)

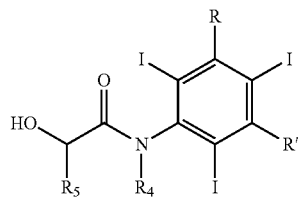

(5)

According to the present process for preparing x-ray contrast agents, the electrochemical iodination of steps (a) and (b) is carried out as formerly reported whilst steps (c) and (d), comprehensive of experimental conditions and optional variants thereof, are known in the art as reported, for instance, in the aforementioned patent applications WO 88/09328, WO 97/05097 and WO 00/32561.

Preferably, within the compounds of formula (3), Z is a bromine or chlorine atom. Even more preferably, the instant process may be applied to the preparation of widely known x-ray contrast agents like iopamidol (wherein, respectively, R and R' both represent a —CONH—CH(CH₂OH)₂ group, R⁴ is hydrogen and R⁵ is methyl; see The Merck Index, XIII Ed., 2001, No. 5073) or iomeprol (wherein, respectively, R and R' both represent a —CONH—CH₂—CH(OH)CH₂OH group, R⁴ is methyl and R⁵ is hydrogen; see The Merck Index, XIII Ed., 2001, No. 5071).

Therefore, it is an additional object of the invention a process for the preparation of iopamidol or iomeprol by starting from the compounds of formula (2a) or (2b), respectively, the said compounds of formula (2a) and (2b) being obtained through the electrochemical iodination of compounds (1a) or (1b), respectively, as per steps (a) and (b) of the process of the invention.

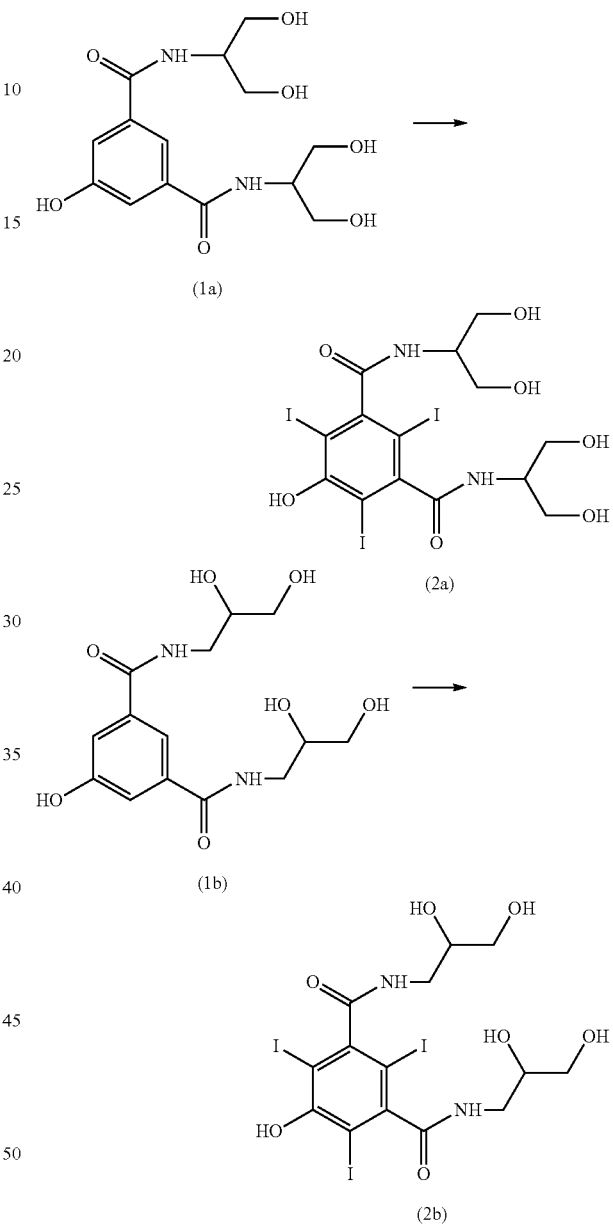

According to an additional aspect of the invention, the instant process may be conveniently employed also for the preparation of suitably substituted anilines bearing given carboxy or carboxyester groups, substantially as set forth below.

Hence, according to an additional embodiment of the invention, it is herewith provided a process for the preparation of 3,5-disubstituted-2,4,6-triiodoanilines of formula (7), which process comprises:

(a) electrochemically generating I⁺ cations from a suitable iodine source; and (b) iodinating 3,5-disubstituted-anilines of formula (6) in the presence of the above I⁺ cations of step (a):

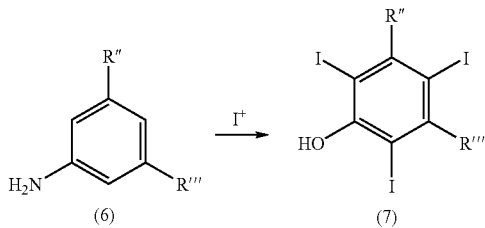

wherein

R" and R'" represent, the same or different from each other, a carboxy —COOH or carboxyester group —COOR$^1$, wherein R$^1$ is a straight or branched C$_1$-C$_6$ alkyl group which is optionally substituted by one or more groups selected from hydroxy, amino, sulphydryl, C$_1$-C$_6$ alkoxy or carboxy, and/or optionally interrupted by one or more divalent groups selected from —NH—, —O—, >C=O, —(C=O)O—, —O(C=O)—, —NH(C=O)—, —(C=O)NH—, >SO or >SO$_2$ groups.

In the present description, unless otherwise provided, within formula (6) and (7) the definitions of R" and R'" and, hence, of R$^1$, are those previously reported.

Preferably, within the above process for preparing the compounds of formula (7), R" and R'" are the same and both represent a group —COOH or —COOR$^1$ wherein R$^1$ is a straight or branched C$_1$-C$_4$ alkyl group.

The above process is carried out by first generating the iodinating source I$^+$ as formerly reported that, in subsequent step (b), allows for the complete triiodination of the aromatic ring in high yields and purity.

Also in this case, the starting materials of formula (6) are known or can be easily prepared according to known methods, for instance by suitably hydrogenating or anyway reducing the corresponding nitroisophthalic acid, optionally to be subsequently functionalized according to conventional techniques for the conversion of carboxy to carboxyester groups.

The compounds of formula (7) thus obtained are useful intermediates for the synthesis of X-ray contrast agents, among which are the aforementioned iopamidol and iomeprol, by working according to methods widely known in the art.

With the aim to better illustrate the present invention, without posing any limitation to it, the following examples are now given.

EXAMPLE 1

Generation of the I$^+$ Solution

A stock solution of iodine in methanol (0.55 M, 10 mL) was introduced in a 100 mL beaker, diluted with methanol (20 mL) and acidified with 0.2 mL 97% H$_2$SO$_4$. A porous crucible (6 μm pore diameter) was partially filled with methanol (2 mL), water (6 mL) and 97% H$_2$SO$_4$ (0.2 mL) and introduced in the beaker. A platinum sheet anode was inserted in the beaker and a graphite cathode was introduced in the crucible. The electrolysis was performed in galvanostatic mode (200 mA/cm$^2$) until the anolyte discolored to light yellow. The obtained solution was used as such in the subsequent iodination reactions.

EXAMPLE 2

Synthesis of 3,5-bis(2,3-dihydroxypropylaminocarbonyl)-2,4,6-triiodophenol

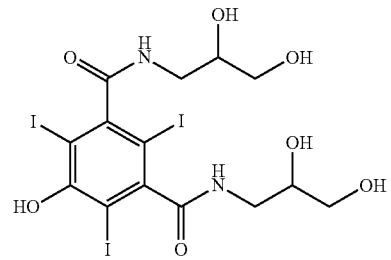 [SMILES: O=C(NCC(O)CO)c1c(I)c(O)c(I)c(C(=O)NCC(O)CO)c1I]

3,5-Bis(2,3-dihydroxypropylaminocarbonyl)-phenol (56.5 mg, 0.17 mmol) was added in a round bottomed flask containing the I$^+$ solution (obtained by working as described in Example 1, from 1.55 mmol I$_2$ and 50 mL MeOH). The reaction mixture was refluxed for 1 hour. An additional amount of 3,5-bis(2,3-dihydroxypropylaminocarbonyl)-phenol (56.5 mg, 0.17 mmol) was then added and the solution was refluxed for 1 hour. A third portion of 3,5-bis(2,3-dihydroxypropylaminocarbonyl)-phenol was finally added (56.5 mg, 0.17 mmol) and the solution was refluxed until complete conversion was observed. After cooling, KI (257 mg, 1.55 mmol) was added and a saturated aqueous solution of Na$_2$SO$_3$ was added dropwise until the solution became pale yellow.

Methanol was removed under reduced pressure and the yellow residue was purified with an Amberlite® XAD 1600 column by elution with water (100 mL) until salts were completely removed and then with water/acetone 8/2 (100 mL).

Yield: 300 mg, 82%.

Spectral Data $^1$H-NMR (D$_2$O, 300 MHz, 298K)

| |
|---|
| 4.00 ppm b quint[2H] |
| 3.74 ppm dd[2H] J$_1$ = 11.6 Hz J$_2$ = 3.7 Hz |
| 3.62 ppm dd[2H] J$_1$ = 11.8 Hz J$_2$ = 6.6 Hz |
| 3.56-3.36 ppm m[4H] |

$^{13}$C-NMR (D$_2$O, 75.4 MHz, 298K)

| |
|---|
| 172.6 ppm [C] |
| 156.0 ppm [C] |
| 148.2 ppm [C] |
| 85.3 ppm [C] |
| 78.9 ppm [C] |
| 70.5 ppm [CH] |
| 64.4 ppm [CH$_2$] |
| 42.9 ppm [CH$_2$] |

EXAMPLE 3

Synthesis of 3,5-bis(1-hydroxymethyl-2-hydroxy-ethylaminocarbonyl)-2,4,6-triiodophenol

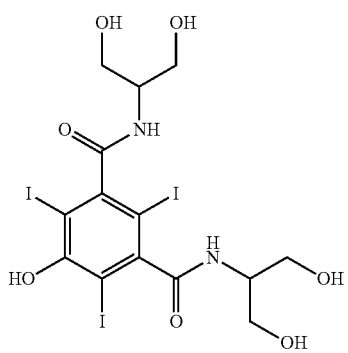 [SMILES: O=C(NC(CO)CO)c1c(I)c(O)c(I)c(C(=O)NC(CO)CO)c1I]

3,5-Bis(1-hydroxymethyl-2-hydroxyethylaminocarbonyl)-phenol (56.5 mg, 0.17 mmol) was added in a round bottomed flask containing the I$^+$ solution (obtained by working as described in Example 1, from 1.55 mmol I$_2$ and 50 mL MeOH).

The reaction mixture was refluxed for 1 hour. An additional amount of the above phenol derivative (56.5 mg, 0.17 mmol) was then added and the solution was refluxed for 1 hour. A third portion of the above phenol derivative was finally added (56.5 mg, 0.17 mmol) and the solution was refluxed until complete conversion was observed. After cooling, KI (257 mg, 1.55 mmol) was added and a saturated aqueous solution of Na$_2$SO$_3$ was added dropwise until the solution became pale yellow.

Methanol was removed under reduced pressure and the yellow residue was purified with an Amberlite® XAD 1600 column by elution with water (100 mL) until salts were completely removed and then with water/acetone 8/2 (100 mL).

Yield: 200 mg, 55%.

Spectral Data $^1$H-NMR (D$_2$O, 300 MHz, 298K)

| | | |
|---|---|---|
| 4.11 ppm | quint[2H] | J = 5.2 Hz |
| 3.85-3.70 ppm | m[8H] | |

$^{13}$C-NMR (D$_2$O, 75.4 MHz, 298K)

| | |
|---|---|
| 172.1 ppm | [C] |
| 156.0 ppm | [C] |
| 148.4 ppm | [C] |
| 85.1 ppm | [C] |
| 78.7 ppm | [C] |
| 60.0 ppm | [CH$_2$] |
| 53.2 ppm | [CH] |

EXAMPLE 4

Synthesis of 3,5-bis(n-butoxycarbonyl)-2,4,6-triiodophenol

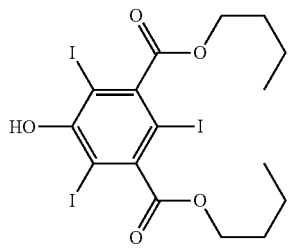 [SMILES: CCCCOC(=O)c1c(I)c(O)c(I)c(C(=O)OCCCC)c1I]

In a round bottomed flask containing the I$^+$ solution (obtained by working as described in Example 1, from 0.78 mmol I$_2$ and 50 mL MeOH), 3,5-bis(n-butoxycarbonyl)-phenol (25.0 mg, 0.085 mmol) was added. The solution obtained was refluxed for 1 hour. An additional amount of the above phenol derivative was then added (25.0 mg, 0.085 mmol) and the solution was refluxed for 1 hour. A third portion of the above phenol derivative was finally added (25.0 mg, 0.085 mmol) and the solution was refluxed 7 h, until complete conversion was observed.

After cooling, KI (125 mg, 0.76 mmol) was added and a saturated aqueous solution of Na$_2$SO$_3$ was dropped until the solution became pale yellow.

Methanol was removed under reduced pressure and the yellow solution so obtained was diluted with water and extracted with AcOEt (3×20 mL). The organic phase was dried over Na$_2$SO$_4$ and evaporated under reduced pressure. The black residue was purified by flash chromatography onto silica gel (eluent: 9 petroleum ether/0.5 isopropanol/0.5 AcOEt).

Yield: 100 mg, 58%.

Spectral Data $^1$H-NMR (CDCl$_3$, 300 MHz, 298K)

| | | |
|---|---|---|
| 6.23 ppm | bs[1H] | |
| 4.36 ppm | t[4H] | J = 6.6 Hz |
| 1.75 ppm | quint[4H] | J = 6.7 Hz |
| 1.47 ppm | sext[4H] | J = 7.4 Hz |
| 0.95 ppm | t[6H] | J = 7.4 Hz |

$^{13}$C-NMR (CDCl$_3$, 75.4 MHz, 298K)

| | |
|---|---|
| 167.8 ppm | [C] |
| 154.7 ppm | [C] |
| 147.9 ppm | [C] |
| 80.8 ppm | [C] |
| 76.4 ppm | [C] |
| 66.8 ppm | [CH$_2$] |
| 30.3 ppm | [CH$_2$] |
| 19.3 ppm | [CH$_2$] |
| 13.7 ppm | [CH$_3$] |

EXAMPLE 5

Synthesis of
3,5-bis(methoxycarbonyl)-2,4,6-triiodophenol

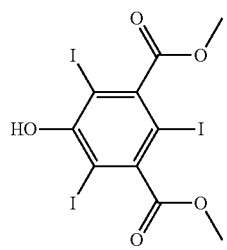 [SMILES: COC(=O)c1c(I)c(O)c(I)c(C(=O)OC)c1I]

In a round bottomed flask containing the I$^+$ solution (obtained by working as described in Example 1, from 0.78 mmol I$_2$ and 50 mL MeOH), 3,5-bis(methoxycarbonyl)-phenol (53.0 mg, 0.085 mmol) was added. The solution obtained was refluxed for 1 hour. An additional amount of the above phenol derivative was then added (53.0 mg, 0.085 mmol) and the solution was refluxed for 1 hour. A third portion of the above phenol solution was finally added (53.0 mg, 0.085 mmol) and the solution was refluxed 10 h, until complete conversion was observed.

After cooling, KI (125 mg, 0.76 mmol) was added and a saturated aqueous solution of Na$_2$SO$_3$ was dropped until the solution became pale yellow.

Methanol was removed under reduced pressure and the yellow solution so obtained was diluted with water and extracted with AcOEt (3×20 mL). The organic phase was dried over Na$_2$SO$_4$ and evaporated under reduced pressure. The black residue was purified with flash chromatography onto silica gel (eluent: 9 petroleum benzine/0.5 isopropanol/0.5 AcOEt).

Yield: 90 mg, 60%.
Spectral Data
$^1$H-NMR (CDCl$_3$, 300 MHz, 298K)

| 6.23 ppm | bs[1H] |
| 3.95 ppm | s[6H] |

$^{13}$C-NMR (CDCl$_3$, 75.4 MHz, 298K)

| 168.1 ppm | [C] |
| 154.8 ppm | [C] |
| 147.7 ppm | [C] |
| 81.1 ppm | [C] |
| 76.4 ppm | [C] |
| 53.6 ppm | [CH$_3$] |

COMPARATIVE EXAMPLE 1

Iodination of Phenol

In a round bottomed flask containing the I$^+$ solution (obtained in Example 1 from 0.78 mmol I$_2$ and 50 mL MeOH), phenol (24.4 mg, 0.26 mmol) was added. The reaction mixture was refluxed for 5 h. After cooling, KI (131 mg, 0.79 mmol) was added and a saturated aqueous Na$_2$SO$_3$ solution was added dropwise.

Methanol was removed under reduced pressure and the yellow solution so obtained was diluted with water and extracted with AcOEt (3×20 mL). The organic phase was dried over Na$_2$SO$_4$ and evaporated under reduced pressure and the brown residue was charged on a flash chromatography column and eluted with 9 petroleum benzine/1 AcOEt.

Yield: 25 mg, 21%.
Spectral Data

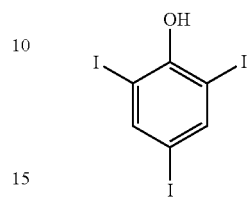

$^1$H-NMR (DMSO-d$_6$+D$_2$O, 300 MHz, 298K)

| 8.01 ppm | s[2H] |

$^{13}$C-NMR (DMSO-d$_6$+D$_2$O, 75.4 MHz, 298K)

| 155.8 ppm | [C] |
| 145.8 ppm | [CH] |
| 88.5 ppm | [C] |
| 85.0 ppm | [C] |

ESI-MS (Negative Mode)
Calc. for C$_6$H$_3$I$_3$O: 471.7 u.m.a.
Found: 471.1 (M-H$^+$), 964.4 (M+Na$^+$-2H$^+$)

In subsequent fractions, more polar byproducts were collected, among which 2-iodohydroquinone and a diiodobiphenol.

COMPARATIVE EXAMPLE 2

Iodination of Pyrogallol

In a round bottomed flask containing the I$^+$ solution (obtained as in Example 1 from 0.78 mmol I$_2$ and 50 mL MeOH), pyrogallol (32 mg, 0.26 mmol) was added. The reaction mixture was refluxed for 3 h. After cooling, KI (131 mg, 0.79 mmol) was added and a saturated aqueous Na$_2$SO$_3$ solution was added dropwise.

Methanol was removed under reduced pressure and the yellow solution so obtained was diluted with water and extracted with AcOEt (3×20 mL). The organic phase was dried over Na$_2$SO$_4$ and evaporated under reduced pressure. The chromatographic analysis of the brown residue so obtained showed a complex and inseparable mixture of oxidized and iodinated byproducts.

COMPARATIVE EXAMPLE 3

Electrochemical Generation of I$^+$ in a Hydroalcoholic Medium

The electrochemical iodination apparatus consisted of a cell composed of:
  an anode compartment with a platinum anode (foil, 3 cm$^2$) and a magnetic stirring bar;
  a cathode compartment with a stainless steel cathode (plate, 8 cm$^2$).

The two compartments were separated by a porous glass frit (average pore size 6 μm). In the anode compartment it was placed a 0.15 M solution of NaBF$_4$ in methanol/water (50/50, 40 mL) and iodine (762 mg, 3 mmol) was added therein with vigorous stirring. Owing to the low solubility of iodine in the mixture, a large portion of it was still present, as a precipitate, at the bottom of the anode compartment; the mixture showed a pale orange colour. pH was adjusted to 1.5 by using a 40% aqueous solution of $HBF_4$.

In the cathode compartment, it was placed a 0.15 M solution of $NaBF_4$ in methanol/water (50/50, 15 mL).

A constant current of 400 mA was applied. After about 30 minutes, the current began to decrease and after about 40 minutes the current dropped to ~60 mA at the maximum power supply voltage of 31.6 V. The solution was yellow and the major portion of the starting iodine was still present at the bottom of the anolyte compartment. The solid iodine was recovered by filtration, washed with water and dried, weighing 678 mg (89% recovery of unreacted iodine).

The invention claimed is:

1. A process for the preparation of 3,5-disubstituted-2,4,6-triiodophenols of formula (2), which process comprises:
   (a) electrochemically generating $I^+$ cations at the anode from a suitable iodine source selected from the group consisting of molecular $I_2$, sodium or potassium iodide, hydroiodic acid and combinations thereof in an organic polar solvent selected from the group consisting of acetonitrile, $C_1$-$C_4$ alcohols, and mixtures thereof; and
   (b) iodinating 3,5-disubstituted-phenols of formula (1) in the presence of the $I^+$ cations of step (a):

wherein
R and R' are, independently, selected from the group consisting of —COOH, —$COOR^1$, —$CONH_2$, —$CONHR^1$ and —$CONR^2R^3$); wherein $R^1$, $R^2$ and $R^3$ are, independently, a straight or branched $C_1$-$C_6$ alkyl group which is optionally substituted by one or more groups selected from hydroxy, amino, sulphydryl, $C_1$-$C_6$ alkoxy or carboxy, and/or optionally interrupted by one or more divalent groups selected from —NH—, —O—, —(C=O)—, —(C=O)O—, —O(C=O)—, —NH(C=O)—, —(C=O)NH—, —S(O)— or —$S(O_2)$—groups.

2. A process according to claim 1 wherein R and R' are, independently, selected from the group consisting of —COOH, —$COOR^1$, —$CONH_2$, —$CONHR^1$ and —$CONR^2R^3$, wherein $R^1$, $R^2$ and $R^3$ are, independently, a straight or branched $C_1$-$C_4$ alkyl group optionally substituted by one or more hydroxy groups.

3. A process according to claim 2 wherein R and R' are, independently, selected from the group consisting of:
   —OOH,
   —$COOCH_3$,
   —$COO(CH_2)_3$—$CH_3$,
   —$CONH_2$,
   —$CONHCH_3$,
   —$CONHCH_2$—CH(OH)—$CH_2$(OH), and
   —$CONHCH[CH_2OH]_2$.

4. A process according to claim 1 wherein $I^+$ cations are generated in situ from molecular $I_2$.

5. A process according to claim 1 wherein the solvent of step (a) is methanol.

6. A process according to claim 1 wherein, for the electrochemical generation of $I^+$ cations at the anode in step (a), an anode potential of from 1 to 3 V versus SCE is applied.

7. A process according to claim 6 wherein the anode potential is from 1.2 to 1.8 V versus SCE.

8. A process according to claim 1 wherein the electrochemical generation of $I^+$ cations at the anode in step (a), is carried out in a galvanostatic mode by passing a constant current of 1-500 $mA/cm^2$ through the solution.

9. A process according to claim 1 wherein step (b) is carried out in a separate reactor.

10. A process according to claim 9 wherein the resulting solution of step (a) is transferred to a separate reactor and contacted with the compound of formula (1) or a solution thereof.

11. A process according to claim 1, further comprising:
    (c) reacting the compound of formula (2), either as such or wherein the hydroxy group on the benzene ring is present as alkali or alkali-earth metal salt, with a compound of formula (3)

$$R_4HN(C=O)CH(R_5)Z \qquad (3)$$

wherein $R_4$ and $R_5$ are, independently, hydrogen or a straight or branched $C_1$-$C_6$alkyl group optionally substituted by one or more hydroxy or $C_1$-$C_6$ alkoxy groups and Z is a halogen atom or any suitable leaving group; so as to obtain a compound of formula (4)

wherein R, R', $R_4$ and $R_5$ have the above reported meanings; and
    (d) subjecting the compound of formula (4) to Smile's rearrangement in the presence of bases, so as to obtain the final compound of formula (5)

12. A process according to claim 10 wherein Z is a bromine or chlorine atom.

13. A process according to any one of claims 10 or 11 wherein both R and R' are a —CONH—$CH(CH_2OH)_2$ group, $R_4$ is hydrogen and $R_5$ is methyl and compound (5) is Iopamidol.

14. A process according to any one of claims 10 or 11 wherein both R and R' are a —CONH—$CH_2$—CH(OH)$CH_2OH$ group, $R_4$ is methyl and $R_5$ is hydrogen and compound (5) is Iomeprol.

* * * * *

UNITED STATES PATENT AND TRADEMARK OFFICE
CERTIFICATE OF CORRECTION

PATENT NO. : 9,193,659 B2  
APPLICATION NO. : 12/918001  
DATED : November 24, 2015  
INVENTOR(S) : Giovenzana et al.

Page 1 of 1

It is certified that error appears in the above-identified patent and that said Letters Patent is hereby corrected as shown below:

ON THE TITLE PAGE  
ITEM (57) IN THE ABSTRACT  
Formula (7), that portion of the formula reading "HO" should read -- $H_2N$ --.

IN THE CLAIMS  
Column 15, claim 1, line 43 "and $–CONR^2R^3$); wherein" should be -- and $–CONR^2R^3$; wherein --; claim 3, line 59, "—OOH" should be -- —COOH --.

Column 16, claim 12, line 57 "according to claim 10" should be -- according to claim 11 --; claim 13, line 59 "according to any one of claims 10 or 11" should be -- according to any one of claims 11 or 12 --; claim 14, line 63 "according to anyone of claims 10 or 11" should be -- according to any one of claims 11 or 12 --.

Signed and Sealed this  
Twenty-fourth Day of May, 2016

Michelle K. Lee  
*Director of the United States Patent and Trademark Office*